United States Patent [19]

Carlsson

[11] Patent Number: 5,725,533
[45] Date of Patent: Mar. 10, 1998

[54] TORSIONAL TIGHTENER FOR BONE ANCHORING OR IMPLANT ELEMENTS/ TOOLS

[75] Inventor: Lennart Carlsson, Mölndal, Sweden

[73] Assignee: Nobel Biocare AB, Goteborg, Sweden

[21] Appl. No.: 745,313

[22] Filed: Nov. 12, 1996

Related U.S. Application Data

[63] Continuation of Ser. No. 386,180, Feb. 9, 1995, abandoned, which is a continuation of Ser. No. 109,110, Aug. 19, 1993, abandoned, which is a continuation of Ser. No. 665,765, Mar. 8, 1991, abandoned.

[30] Foreign Application Priority Data

Mar. 9, 1990 [SE] Sweden .................. 9000836

[51] Int. Cl.⁶ .................. A61B 17/58
[52] U.S. Cl. .................. 606/101; 606/104
[58] Field of Search .................. 433/141, 146, 433/147, 173, 174; 606/104, 101; 81/429, 467, 469, 473, 479; 192/141, 142 R, 150; 173/176, 181–183, 20, 2; 73/862.21, 862.22, 862.23, 862.24

[56] References Cited

U.S. PATENT DOCUMENTS

| | | | |
|---|---|---|---|
| 3,174,559 | 3/1965 | Vaughn | 173/181 |
| 3,693,726 | 9/1972 | Hörnig et al. | 73/862.24 X |
| 3,825,912 | 7/1974 | Wiese et al. | 81/467 X |
| 3,934,629 | 1/1976 | Boman | 81/429 |
| 3,993,145 | 11/1976 | Findeli | 173/176 |
| 4,091,451 | 5/1978 | Weiner et al. | 173/182 X |
| 4,106,176 | 8/1978 | Rice et al. | 173/182 X |
| 4,244,434 | 1/1981 | Wilson | 81/467 X |
| 4,359,506 | 11/1982 | Cordey | 81/467 X |
| 4,359,906 | 11/1982 | Cordey | 81/467 |
| 4,397,196 | 8/1983 | Lemelson | 73/862.23 |
| 4,418,765 | 12/1983 | Moir et al. | 173/182 |
| 4,562,389 | 12/1985 | Jundt et al. | 81/469 X |
| 4,562,746 | 1/1986 | Petit | 73/862.23 |
| 4,685,050 | 8/1987 | Pulter et al. | 81/467 X |
| 4,759,225 | 7/1988 | Reynertson et al. | 73/862.21 |
| 4,828,049 | 5/1989 | Preis | 173/163 |
| 4,883,130 | 11/1989 | Dixon | 81/467 X |

(List continued on next page.)

FOREIGN PATENT DOCUMENTS

| | | | |
|---|---|---|---|
| 0024480 | 3/1981 | European Pat. Off. | 173/20 |
| 3324333 | 1/1985 | Germany | 81/479 |
| 2190864 | 12/1987 | United Kingdom | 81/473 |
| 2195569 | 4/1988 | United Kingdom | 81/467 |
| 2198983 | 6/1988 | United Kingdom | 81/467 |

*Primary Examiner*—Michael Buiz
*Assistant Examiner*—Kevin Truong
*Attorney, Agent, or Firm*—Pollock, Vande Sande & Priddy

[57] ABSTRACT

A compact torsional tightener system for anchoring tools or implants in bone or dentine or elements in implants anchored in bone or dentine sufficiently compact to be inserted into a patient's mouth includes a transformerless electric motor with a small rotating mass operating at a speed of about 10,000 to about 15,000 revolutions per minute and powered by an energy supply circuit. A gear part converts the speed of the motor to a slower speed. A controller senses the torque from the tool or element being anchored and interrupts the energy supply circuit at the predetermined parameter value such that the controller controls the rotational inertia in the motor, motor shaft, and element or tool so as to permit the motor, motor shaft and tool or element to rotate beyond a point where they are located when the electrical energy is interrupted to bring about a torsional tightening moment near a preselected optimal point substannially near but not exceeding a breaking point of the weakest member of the element, tools, or implants. A majority of the increasing torsional resistance from the bone or dentine is imparted to the element, tool, or implant by the implant, bone or dentine over during ½ to ½ turn of the element, tool, or implant. The energy supply circuit is interrupted such that the effect of rotational energy in the tightener after the interruption causes the tool or element to rotate by at most 10%.

16 Claims, 3 Drawing Sheets

U.S. PATENT DOCUMENTS

| | | | |
|---|---|---|---|
| 4,894,767 | 1/1990 | Doniwa | 173/183 X |
| 4,898,249 | 2/1990 | Ohmori | 173/176 |
| 4,908,926 | 3/1990 | Takeshima et al. | 81/469 |
| 4,987,806 | 1/1991 | Lehnert | 81/469 |
| 4,991,473 | 2/1991 | Gotman | 81/467 X |
| 5,014,793 | 5/1991 | Germanton et al. | 81/473 X |
| 5,044,234 | 9/1991 | Cheng | 81/469 |
| 5,060,772 | 10/1991 | Anders et al. | 192/150 X |
| 5,062,491 | 11/1991 | Tukeshima et al. | 173/181 |

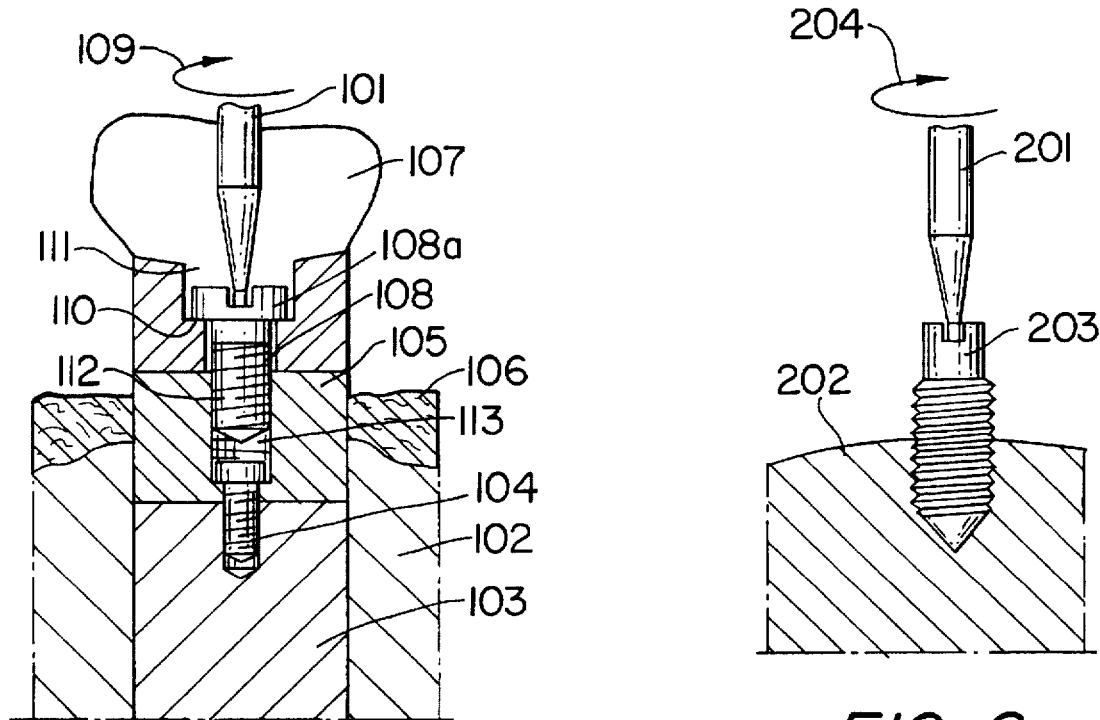
FIG. 1
FIG. 2
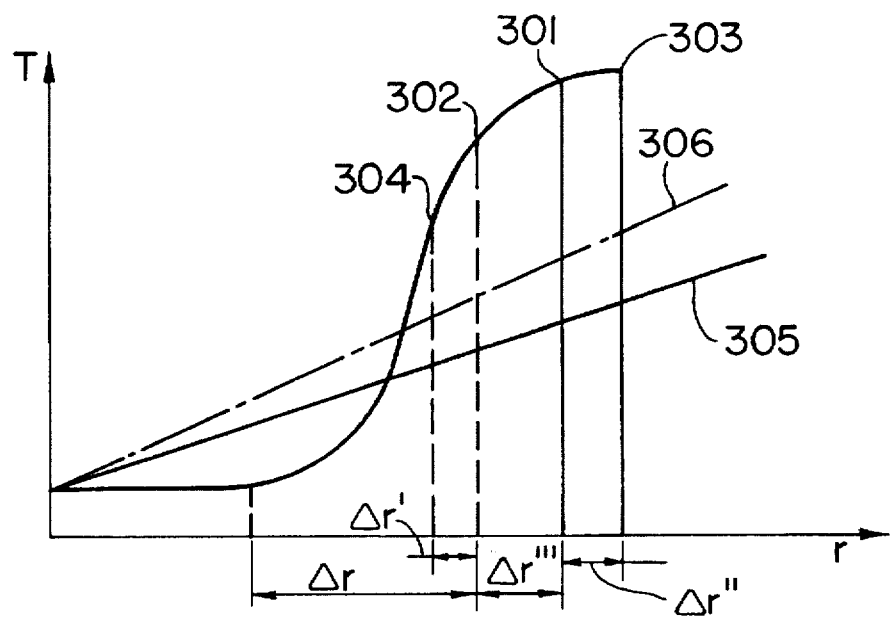
FIG. 3

TORSIONAL TIGHTENER FOR BONE ANCHORING OR IMPLANT ELEMENTS/TOOLS

This application is a continuation of U.S. patent application Ser. No. 08/386,180, filed Feb. 9, 1995 now abandoned, which is a continuation of U.S. patent application Ser. No. 08/109,110 filed Aug. 19, 1993, now abandoned, which was a continuation of application Ser. No. 07/665,765 filed on Mar. 8, 1991, now abandoned.

FIELD OF THE INVENTION

The present invention relates to a torsional tightener for elements/tools for anchoring in the bone or anchoring in implants anchored in the bone, especially dentine or dental implants.

BACKGROUND OF THE INVENTION

The torsional tightener of the present invention is of the type which is releasable at a previously set or desired torque.

Such torsional tighteners typically comprise an electric motor operating at high speed with a connected unit to decrease the speed, and a torsional tightening part, or screwdriver actuated by the unit and cooperating with the element to be anchored. The electric motor can be supplied with electrical energy which increases as a function of a torsional resistance from the element/tool growing during the process of tightening of the element/tool. Moreover, the set torque can be determined by means of a predetermined parameter value for the supplied electrical energy.

In connection with the anchoring of elements in bone or the tightening of screws in implants anchored in bone, it is already known to use tighteners which can be set for different or varying torques. In this respect it is known to use torque tighteners which are actuated by electrical energy and by manual force. In connection with electrical torque tighteners, it is also known to use a unit for indicating and setting the different torque tightening values.

However, the tightening of screws in implants anchored in bone presupposes that screwing-in is effected with torques which it must be possible to set exactly. There must be a secure anchoring of the screw, which in turn requires that the yield point, or elasticity, of the screw material must be attained but not exceeded. The range for an optimal torsional action in accordance with the above is relatively narrow. In addition, the torque effected with the tightener is relatively great, so that for this reason it may be difficult to distinguish the necessary sensitivity upon torsional tightening.

The tool/instrument will be used for working in the mouth of a patient, and this, together with the requirement for a relatively high torsional resistance, rules out manual torque activation, in which respect there may additionally be difficulties in achieving a continuous monitoring of the effected torque during the tightening process from the indication point of view.

When screwing an implant, it may be desirable to obtain a suitable indication of the state of softness or hardness of the bone or dentine. It may therefore be of value to obtain an indication of the torque effected upon screwing-in, this torque corresponding to the torsional resistance transmitted to the element/tool from the bone or dentine.

It is also desirable if the design of the tightener can be included under standard forms already available in the field. The tool can be of a construction in which an angle-piece or hand-piece (gear piece) of standard design can be used.

SUMMARY OF THE INVENTION

The present invention proposes a torsional tightener which solves, the problems mentioned above. There are two alternative designs for achieving a well-defined set/settable torque value for a torsional tightener according to the invention. In the first design, the energy supply circuit of the electric motor can be interrupted at the predetermined parameter value mentioned in the introduction, and the interruption and the rotational energy in the rotating parts of the torsional tightener after interruption are designed to bring about a torsional tightening moment which is situated at or near an optimal or desired point on the particular moment curve for the tightening in question. In the second main design) the torsional tightening part is connected to the unit, which decreases the speed, via a disconnection part which can be actuated at the predeterminable parameter value, which is thus chosen to bring about a torsional tightening moment which is situated at or near an optimal or desired point on the particular moment curve for the tightening in question.

The interruption of the electrical energy to the electric motor is designed to occur close to the optimal or desired point on the moment curve, and the rotational energy which exists immediately after the interruption has only a marginal effect on the torque value finally obtained. In a preferred embodiment, the high-speed electric motor (10000–15000 rpm) is designed with a small rotating weight, which means that the rotational energy remaining after interruption can be kept low. For example, in a case where the growing torsional resistance from the element/tool is effected principally during ¼–½ a rotational turn, the effect from the remaining rotational energy is over only a few degrees of the total turn.

According to one embodiment of the invention, a unit is used or included for setting and indicating the torque values. Thus, for example, a liquid-crystal gauge can be used for indicating the torsional resistance effected by the tightener at each moment in time. Close to the liquid-crystal gauge there are elements for indicating the set torque value at which the release of the tightener will take place. When the tightener has reached the set value, the liquid-crystal gauge has been activated close to the element in question for the set values, the result of this being that an observer can continuously monitor the torque values up to the value in question. In one embodiment, a special indication is obtained when the set value has been reached. The setting and indicating unit can also be designed with members for setting two or more output speeds of the torsion-effecting or screwdriver part.

In one embodiment, the energy supply circuit of the electric motor is sensed by a sensing circuit. The latter is actuable when the current in the energy supply circuit reaches a predetermined current value. At such value, the sensing circuit generates and sends an interrupt signal or break signal to the interrupting or breaking members of the energy supply circuit of the electric motor. In addition, the motor can be short-circuited in order to shorten the stoppage time.

By virtue of the features mentioned above, the torsional tightener can operate with exact release of the set torque values. The torque tightener can be tailored to a specific purpose, for example, tightening screws of, for example, gold or titanium in implants anchored in bone. Screw-shaped implants, or thread taps for such implants, can be anchored in or shape bone with the said exactness of release. The connection to one or more indicating and/or setting units makes it possible to obtain, in an extremely simple manner, continuous information on, for example, the state of the bone/dentine in which implanting is to take place.

3

BRIEF DESCRIPTION OF THE DRAWINGS

A presently proposed embodiment of an arrangement having the features characteristic of the invention will be described hereinbelow with reference to the attached drawings, in which FIG. 1 shows a vertical cross-section of the anchoring of a prosthesis, specifically, a dental crown in a cap which in turn is screwed securely in an implant anchored in the dentine;

FIG. 2 shows a vertical cross-section of the threading of the dentine with the aid of a thread tap which is under the torsional influence of a tightening member;

FIG. 3 shows a torque-speed diagram;

DETAILED DESCRIPTION OF THE PREFERRED EMBODIMENT

Figure 4:
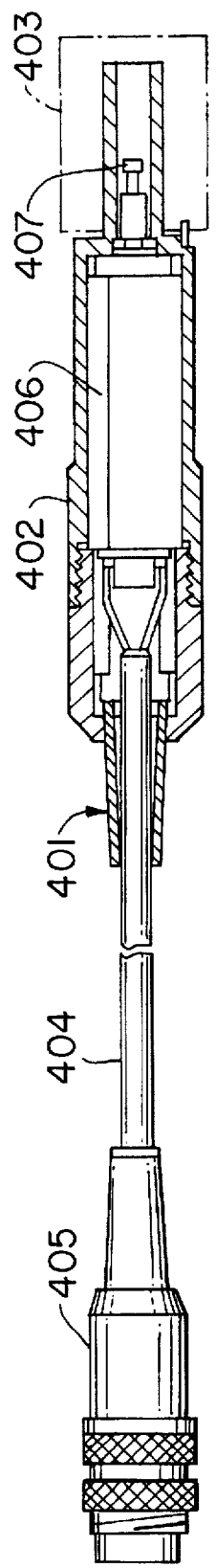
FIG. 4 shows a longitudinal cross-section of a torsional tightener with a connector for electrical connection.

FIG. 1 and 2 show two embodiments of the present invention in which a torsional tightener/screwdriver 101, 201 with built in torque setting may be used. The dentine is symbolized by 102, 202. In FIG. 1, an implant is indicated as 103 and a cap anchored to the implant by a screw 104 is indicated as 105. The skin covering is symbolized by 106. A prosthesis 107, for example, a tooth or cap may be screwed securely in the 105 with a screw 108 whose direction of screwing is shown by 109.

The screwdriver 201 is used for a thread tap 203, by means of which a thread for the implant is made in the dentine 202. The direction of rotation of the screwdriver 201 is shown by 204.

A torque-speed curve for the case according to FIG. 1 is shown by 301. A range Δr indicates the actual process of tightening of the screw 108, during which process the underside of the head 108a of the screw 108 cooperates with a bottom surface 110 in a recess 111 of the prosthesis. In addition to this cooperation, there is also cooperation between the thread 112 of the screw and the thread 113 of the recess. The tightening of the screw 108 for its secure anchoring to the prosthesis 107 and the cap 105 assumes that a predetermined point 302 on the curve 301 is reached, at which point a certain stressing of the screw material has taken place. A point 303 indicates the breaking limit for the screw material. The range Δr represents ¼–½ of a turn r.

According to the present invention, an electrical energy supply, described below, will be interrupted when the tightening process is at a point 304. The remaining rotational energy in the tightening tool is able to influence the tightening in such a way that it is possible to arrive at or nearer the point 302 than is shown in the figure. The requirement is to avoid unduly reaching close to or exceeding the breaking limit 303. Δr' is the angle of rotation range which will preferably be accomplished, and in the exemplary embodiment the range represents about 10° of a turn. The angle of rotation range Δr" is a prohibited range, while Δr'"

4 is the maximum permitted range beyond point 302. Δr'" is about 15° and Δ4" is about 10°.

The straight-line curves 305 and 306 apply to the case according to FIG. 2. The slopes of the straight-line curves symbolise the stability in the dentine 202, in which respect 305 relates to a case with softer dentine than 306.

FIG. 4 shows an embodiment of a torsional tightener comprising a driving motor 402, a gear part 403 driven by the latter, an electric motor connection line 404 and a connector 405. The part 402 comprises an electric motor 406 which is of the Kommunterad d.c. motor type (Escap HA 16, 16M 11 210 2430), which is a transformerless motor. The output drive shaft of the motor is indicated by 407. The gear part, which is only shown partially, consists of a previously known standard part of the minimotor type.

Figure 5:
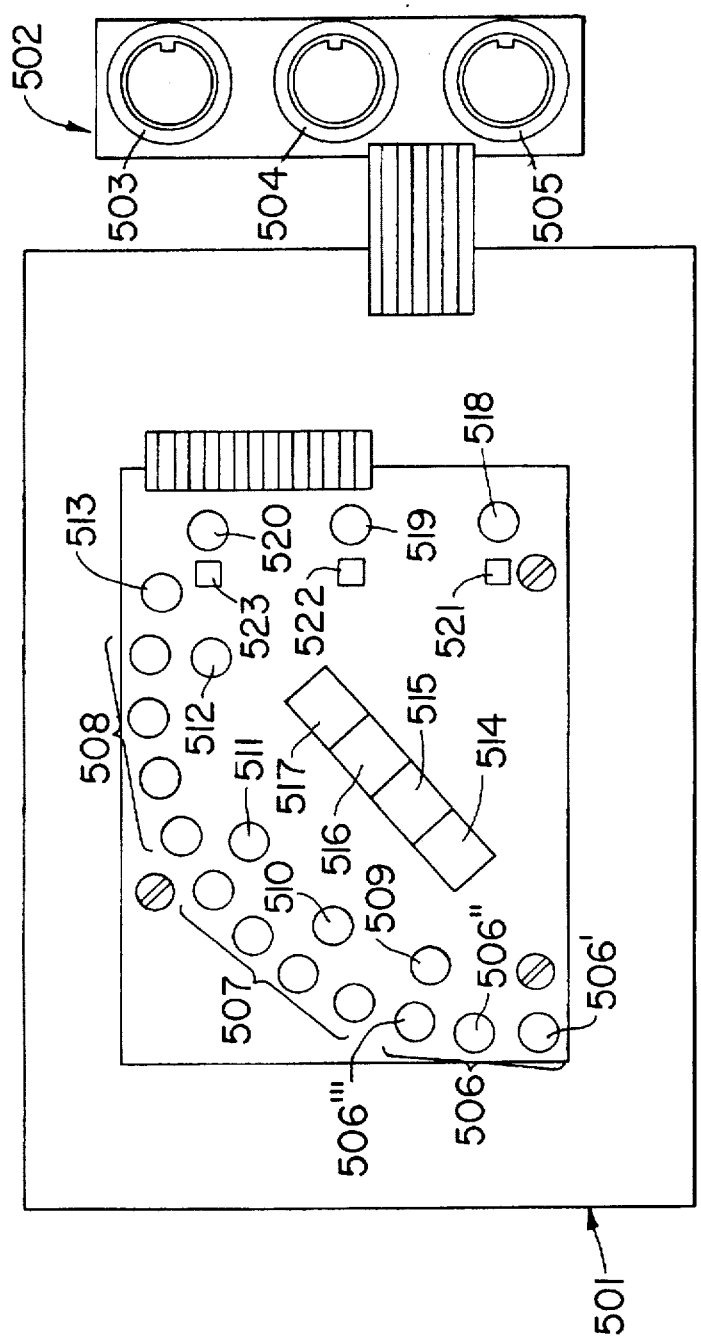
FIG. 5 shows a horizontal view of a setting and indicating member for the connector according to FIG. 4.

FIG. 5 shows in principle the combined setting and actuating unit, which also effects the current supply to the electric motor 406. The unit 501 is box-shaped, and its gable part 502 is shown in an upturned position for reasons of clarity. The unit 501 is provided with three connections 503, 504 and 505. One of the connections, for example 504, is intended for the connector 405 in FIG. 4. The other two connections are intended for electricity supply. The unit 501 is provided with a "liquid-crystal" type gauge which, in this embodiment, is made up of a number of optical elements, for example light-emitting diodes, arranged in a row one after the other. The light-emitting diodes of the gauge are divided into three groups 506, 507 and 508. The unit also comprises four indicating members 509, 510, 511 and 512 which can consist of optical indicating elements, for example light-emitting diodes. A further indicating element is indicated by 513. The indicating element 513 indicates when a predetermined value has been reached with the tightener according to FIG. 4. The unit 501 also comprises a number of actuating members 514, 515, 516 and 517 by means of which it is possible to carry out presettings of the torque for the tightener according to FIG. 4. The presettings correspond to the positions indicated by the indicating members 509–512.

The unit also comprises setting and indicating members for different speeds of the output shaft from part 403 of tightener 401. The indicating members for two speeds are shown by 519 and 520, and corresponding actuating members are shown by 522 and 523. The unit 501 also operates with a reverse change-over function comprising an indicating function 518 and actuating member 521. The reversing function can be made in a known manner. The speed-setting achieved using 522, 519 and 523, 520 is also effected in a known manner. One of four predeterminable torque values, at which the he tightener 401 will be releasable, can be set using the particular actuating member in question of actuating members 514–517. When the tightening, for example according to the embodiments in FIGS. 1 and 2, is started, the light-emitting diodes are lit in sequence in gauge 506, 507 and 508. For example, if the value which is indicated by indicating member 509 is set by 514, then the lowermost light-emitting diode 506' is first lit when a torque corresponding to this light-emitting diode has been reached. If a torque corresponding to 506" is reached in the continued torsioning process, this light-emitting diode is also lit, when the torque corresponding to light-emitting diode 506'" is reached, the light 506'" is lit. This value is finally indicated by the light-emitting diode 513 lighting. If the torque value according to light 511 is set using setting member 516, underlying light-emitting diodes are lit in sequence until the torque value according to light-emitting diode 511 is reached, after which the light-emitting diode 513 in the same way indicates the finally reached value, and so on. It is desirable for the part 403 to be able to operate at different speeds, and the unit 501 affords, by means of actuating members 521, 522 and 523, the possibility of setting different values, for example 10 rps, 20 rps and 30 rps. The electric motor 406 operates at a high speed, for example between 10000 and 15000 rps per minute. The part 403 decreases this speed considerable, in a known manner.

Figures 6, 7:
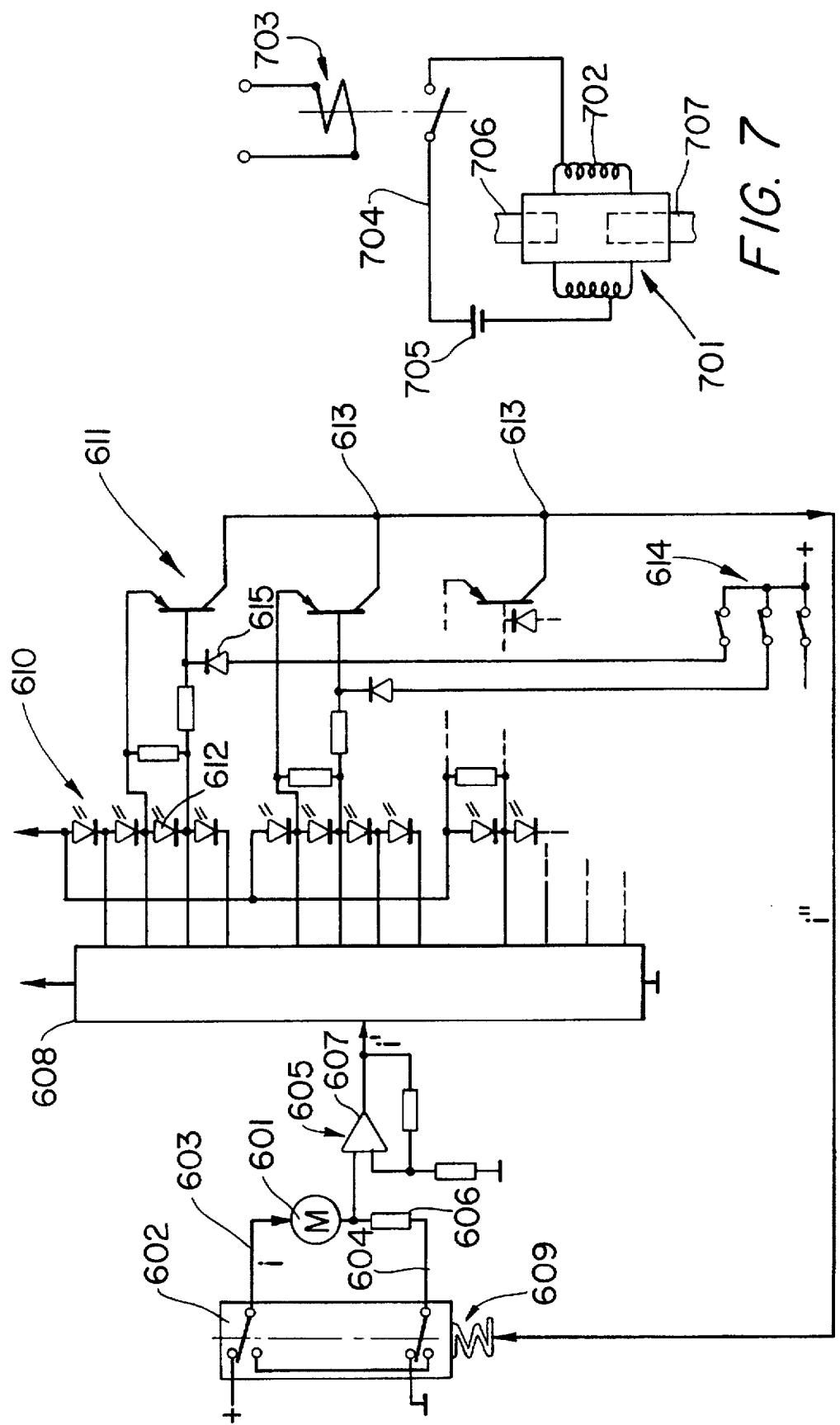
FIG. 6 shows a circuit diagram of the member for sensing the current in the energy supply circuit of an electric motor, the interrupt circuits controlled by the said sensing circuit, and the principle for indicating functions in the unit according to FIG. 5.
FIG. 7 shows a circuit diagram of a disconnection function for a torsional tightener according to FIG. 4.

In FIG. 6, 601 indicates the electric motor described above. The electric motor is connected to a current supply and control circuit 602. The supply lines of the electric motor are indicated by 603 and 604. A sensing circuit 605 is connected to line 604 between the electric motor and a resistor 606 (about 1 ohm). The sensing circuit is provided with an operational amplifier 607 and, connected to this, a control unit 608. The sensing circuit senses the current in the supply circuit 603, 604. When the current assumes a predetermined value which brings about a signal i' of predetermined magnitude at the output of the amplifier 607, a release signal i" is received from the unit 608. This release signal activates an interrupt or break member 609, which interrupts or short-circuits the lines 603, 604. The units 608 and 609 are provided with a restoring function for the member 609, so that the electric motor can receive energy supply for new driving.

The indicating/light-emitting diode stack divided into groups (cf. 506, 507 and 508) is shown by 610 in FIG. 6. In the stack, selected light-emitting diodes, for example the light-emitting diodes which are opposite the indicating members 509, 510, 511 and 512 (FIG. 5), are used for effecting the interrupt signal i" for the member 609 in or at the unit 602.

To each selected light-emitting diode there is allocated a transistor coupling, the lighting/activation of each selected light-emitting diode 612 is detected by the respective transistor coupling 611 which, as a function of the lighting/ activation, initiates the signal i" at its output. All the transistor couplings for the stack 610 are connected to a common output 613 so that any transistor coupling can generate the signal i" when the respective selected light-emitting diode in the stack is lit. The member 609 is activated as long as the signal i" is present, and, when the signal i" ceases, the member 609 assumes the initial position when the motor 601 receives supply current. The activated transistor coupling is deactivated by means of a logic circuit 614 of known type. For deactivating the activated transistor coupling, the logic circuit connects up a diode 615, whose connection results in the deactivation. The logic circuit ensures that only one transistor coupling at a time can be connected and the circuit 614 is controlled from the change-over switches 514, 515, 516 and 517. The lighting and extinguishing of the diodes 509, 510, 511, 512 and 513 can be effected from the unit 608 and as a function of the activation of the actuating members 514, 515, 516 and 517. The light-emitting diodes 509-512 can be designed so as to be actuable by means of the change-over switches 514-517, and the light-emitting diode 513 can be designed so as to be actuated by the output signal from the respective transistor coupling 611.

FIG. 7 relates to a case where the interrupt function, according to FIG. 6 has been replaced with a disconnection function 701. The disconnection function operates with an electromagnet function, whose winding is indicated by 702. This winding receives current supply with the aid of actuation member 703. Actuation member 703 closes an actuation circuit 704, with battery 705 or other energy supply, for the winding 702. When the winding receives current supply, the disconnection comes into operation and the rotating shaft of the gear part, as symbolized by 706, is disconnected from the drive shaft for driving the screwdriver function (cf. 101 in FIG. 1). When activation of the winding (electromagnet) 702 ceases, the shaft parts 706 and 707 come into cooperation, etc.

The invention is not limited to the embodiment shown above by way of example, but can be modified within the scope of the following patent claims and the inventive concept.

I claim:

1. A compact torsional tightener system for anchoring implants in bone or dentine, said torsional tightener system comprising:

a torsional tightener sufficiently compact to be inserted into the mouth of a patient;

a transformerless electric motor with a small rotating mass operating at a speed of about 10.000 to about 15,000 revolutions per minute and powered by an energy supply circuit, said motor imparting a high level of torque to said implants with a high degree of sensitivity over a small range;

a controller for controlling a speed of said motor;

a selector for selecting an operating range of speeds and torques based upon the hardness of the bone or dentine in which the implants are being anchored;

a torsional tightening part actuated by the motor and cooperating with the implants;

a gear part interconnected with said motor and said torsional tightening part for converting said speed of said motor to a slower speed that is imparted to said torsional tightening part;

an electrical energy supply connected to the electric motor, said electrical energy supply varying the electrical energy supplied to the electric motor as a function of a torsional resistance from the implants;

means for releasing said torsional tightener at a preset torque based upon the rotational mass of the tightener, the structural strength of the implants to be anchored, and the hardness of the bone or dentine in which the implants are to be anchored;

means for determining said preset torque, said determining means including a predetermined parameter value of the supplied electrical energy; and controlling means for sensing the torque from the implants being anchored and for interrupting the energy supply circuit of the electric motor at said predetermined parameter value such that said controlling means controls the rotational inertia in the motor, motor shaft, and implants so as to permit said motor, motor shaft and implants to rotate beyond a point where they are located when the electrical energy is interrupted to bring about a torsional tightening moment near a preselected optimal point substantially near but not exceeding a breaking point of the implants;

wherein a majority of the increasing torsional resistance from the bone or dentine is imparted to the implants by the bone or dentine over ¼ to ½ turn of the implants, and said controlling means interrupts said energy supply circuit such that the effect of the rotational energy after interruption causes said implants to rotate by at most 10°.

2. The torsional tightener system according to claim 1, wherein said controlling means causes the interruption of said energy supply circuit so as to cause a stress to the material making up said implants within the range defined by said preset torque and a point within 10° of rotation of said implants of the breaking point of said implants.

3. The torsional tightener system according to claim 1, further comprising means for setting the preset torque value at which release is desired to take place and means for indicating when the respective preset value is reached.

4. The torsional tightener system according to claim 3, wherein said setting and indicating means include a liquid crystal gauge including first indicating elements arranged successively, said gauge displaying the growing torque effect from the torsional tightener on account of growing torsional resistance from said implants during the process of tightening.

5. The torsional tightener system according to claim 4, further comprising first indicating elements including second optical elements which indicate the value of the set torque, said first indicating elements being arranged close to and alongside said liquid crystal gauge.

6. The torsional tightener system according to claim 4, wherein said setting and indicating means includes a liquid crystal gauge which displays increasing torque on said implants;
- second indicating elements located opposite said first indicating elements are activated in sequence to indicate when the torque from the torsional tightener has reached certain values; and
- a third indicating element at the upper end of the liquid crystal gauge is actuated when said respective preset value has been reached.

7. The torsional tightener system according to claim 3, wherein said system is designed with setting of at least two output speeds for said torsional tightening part.

8. The torsional tightener system according to claim 1, wherein after the interruption of said energy supply circuit by said controlling means and a dissipation of rotational energy resulting in any further rotation of said, implants said implants remains at least 10° away from a breaking point of implants.

9. The torsional tightener system according to claim 1, wherein after the interruption of said energy supply circuit by said controlling means and a dissipation of rotational energy resulting in any further rotation of said, implants said implants remains at least 10° away from a breaking point of a weakest member of the group consisting of: said bone and said dentine.

10. The torsional tightener system according to claim 1, wherein the motor shaft and implants rotate beyond a point where they are located when the electrical energy is interrupted to bring about a torsional tightening moment near a preselected optimal point substantially near but not exceeding the breaking point of the hardness of the bone or dentine.

11. A compact torsional tightener system for anchoring elements in implants anchored in bone or dentine, said torsional tightener system comprising:
- a torsional tightener sufficiently compact to be inserted into the mouth of a patient;
- a transformerless electric motor with a small rotating mass operating at a speed of about 10,000 to about 15,000 revolutions per minute and powered By an energy supply circuit, said motor imparting a high level of torque to said elements with a high degree of sensitivity over a small range, said energy supply circuit including a sensing circuit sensing current supplied to the motor, the sensing circuit being actuable when the current reaches a predetermined value, the sensing circuit causing an interruption of the energy supply circuit upon said current reaching said predetermined value;
- a controller for controlling a speed of said motor;
- a selector for selecting an operating range of speeds and torques based upon the hardness of the material of the implant;
- a torsional tightening part actuated by the motor and cooperating with the elements;
- a gear part interconnected with said motor and said torsional tightening part for converting said speed of said motor to a slower speed that is imparted to said torsional tightening part;
- an electrical energy supply connected to the electric motor, said electrical energy supply varying the electrical energy supplied to the electric motor as a function of a torsional resistance from the elements;
- controlling means for controlling the rotational inertia in the motor, motor shaft, and elements so as to permit said motor, motor shaft and elements to rotate beyond a point where they are located when the electrical energy is interrupted to bring about a torsional tightening moment near a preselected optimal point substantially near but not exceeding the breaking point of said elements;
- wherein a majority of the increasing torsional resistance from the bone or dentine is imparted to the elements over ¼ to ½ turn of said elements and said controlling means interrupts said energy supply circuit such that the effect of the rotational energy after interruption causes said element to rotate by at most 10°.

12. A torsional tightener system according to claim 1, wherein said electrical energy supply, said selector, said controller, said determining means, and said controlling means are in a separate unit from said torsional tightening and said torsional tightener part.

13. A torsional tightener system according to claim 1, wherein said electrical energy supply, said selector, said controller, said determining means, and said controlling means are in a separate unit from said torsional tightener and said torsional tightening part.

14. A torsional tightener for denture use in the mouth of a patient to anchor a threaded fastener in dentine or in implants in dentine, said tightener comprising:
- a transformerless electrical motor having a small rotating mass and operates at about 10000 to 15000 rpm, so as to be able to exert a high level of torque with high sensitivity over a small range;
- an electrical supply that increases electrical energy in response to increasing torsional resistance on the tightener from said fastener;
- means for interrupting said tightener such that the rotational inertia after interruption of the tightener results in the fastener being tightened to a preselected optimum torque near but not exceeding the breaking point of any of the fastener, implant, or dentine;
- whereby said interrupting means relies in the actual torque exerted by the tightener as well as on a predetermined torque, said actual and predetermined torques being based on feedback in the form of increased torsional resistance on the fastener as expressed by increased electrical supply to said motor;
- a reduction gear arranged on an output shaft of the motor between said shaft and said fastener and substantially reducing the output speed of the tightener;
- means for selecting from a range of output torques and speeds of the motor depending upon the breaking point of any of the fastener, implant, or dentine;
- control means for sensing the actual torque of the fastener being anchored and for interrupting the electrical supply to the motor at a predetermined electrical supply value in such a way that when the fastener torque increase effectively occurs within a rotation of about 90° to 180° the rotation of the fastener after interruption of the electrical supply amounts to less than 10°;

means for setting and monitoring speed and torque values, said means including indicating means arranged to visualize the torque development curve;

said electrical supply, said interrupting means, said control means, said selecting means, said setting and monitoring means, and said indicating means are arranged in a separate unit electrically connected to the tightener.

15. A torsional tightener for dental use in the mouth of a patient to anchor a threaded fastener in dentine or in implants in dentine, said tightener comprising:

a transformerless electric motor having a small rotating mass, operating at a speed of about 10,000 to about 15,000 revolutions per minute, and exerting a high level of torque with a high sensitivity over a small range;

an electric energy supply for said motor that increases electrical energy to said motor in response to increasing torsional resistance on said tightener from said fastener;

means for interrupting said electric energy supply such that rotational inertia in said tightener and fastener after interruption of said electric energy supply results in said fastener being tightened to an optimum torque near but not exceeding the breaking point of said fastener, implant, or dentine, said interrupting means interrupting said electrical energy based upon torque exerted by the tightener and a predetermined torque, said exerted torque being expressed in the form of increased electrical supply to said motor;

a reduction gear arranged between an output shaft of the motor and said fastener and substantially reducing an output speed of the tightener;

means for selecting an output torque and output speed of said motor from a range of output torques and output speeds depending upon the composition of said fastener, said implants, and said dentine;

means for controlling said tightener by sensing a torque on said fastener and interrupting said electrical supply at a predetermined electrical supply value such that when said a majority of an increase in said sensed torque occurs within 90° to 180° of the rotation of said tightener, after interruption, said tightener will continue to rotate by less than 10°;

means for setting and monitoring rotational speed and torque of said tightener; and means for visually displaying a torque development curve of said tightener;

wherein said electrical supply, said interrupting means, said control means, said selecting means, said setting and monitoring means, and said indicating means are arranged in a separate unit.

16. A compact torsional tightener system for anchoring tools in bone or dentine, said torsional tightener system comprising:

a torsional tightener sufficiently compact to be inserted into the mouth of a patient;

a transformerless electric motor with a small rotating mass operating at a speed of about 10,000 to about 15,000 revolutions per minute and powered by an energy supply circuit, said motor imparting a high level of torque to said tools with a high degree of sensitivity over a small range;

a controller for controlling a speed of said motor;

a selector for selecting an operating range of speeds and torques based upon the hardens of the bone or dentine in which the tools being anchored;

a torsional tightening part actuated by the motor and cooperating with the tools;

a gear part interconnected with said motor and said torsional tightening part for converting said speed of said motor to a slower speed that is imparted to said torsional tightening part;

an electrical energy supply connected to the electric motor, said electrical energy supply varying the electrical energy supplied to the electric motor as a function of a torsional resistance from the tools;

means for releasing said torsional tightener at a preset torque based upon the rotational mass of the tightener, the structural strength of the tools to be anchored, and the hardness of the bone or dentine in which the tools are to be anchored;

means for determining said preset torque, said determining means including a predetermined parameter value of the supplied electrical energy; and controlling means for sensing the torque from the tools being anchored and for interrupting the energy supply circuit of the electric motor at said predetermined parameter value such that said controlling means controls the rotational inertia in the motor, motor shaft, and tools so as to permit said motor, motor shaft and tools to rotate beyond a point where they are located when the electrical energy is interrupted to bring about a torsional tightening moment near a preselected optimal point substantially near but not exceeding a breaking point of the tools;

wherein a majority of the increasing torsional resistance from the bone or dentine is imparted to the tools by the bone or dentine over ¼ to ½ turn of the tools, and said controlling means interrupts said energy supply circuit such that the effect of the rotational energy after interruption causes said tools to rotate by at most 10°.

* * * * *